United States Patent
Mancini et al.

(10) Patent No.: US 10,898,392 B2
(45) Date of Patent: *Jan. 26, 2021

(54) BODY FLUID SENSOR PAD

(71) Applicant: Sentine, Inc., Huntsville, AL (US)

(72) Inventors: Ralph Joseph Mancini, Danbury, CT (US); Derek Phelps Gardner, Huntsville, AL (US)

(73) Assignee: Sentine, Inc., Huntsville, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/600,948

(22) Filed: Oct. 14, 2019

(65) Prior Publication Data
US 2020/0038254 A1 Feb. 6, 2020

Related U.S. Application Data

(63) Continuation-in-part of application No. 15/330,222, filed on Aug. 26, 2016, now Pat. No. 10,478,349.

(60) Provisional application No. 62/283,348, filed on Aug. 28, 2015.

(51) Int. Cl.
*A61F 13/42* (2006.01)
*A61F 13/84* (2006.01)
*A61F 13/15* (2006.01)
*A61F 13/514* (2006.01)

(52) U.S. Cl.
CPC .... *A61F 13/42* (2013.01); *A61F 2013/15121* (2013.01); *A61F 2013/424* (2013.01); *A61F 2013/5147* (2013.01); *A61F 2013/8479* (2013.01)

(58) Field of Classification Search
CPC .......................... A61F 13/42; A61F 2013/424
See application file for complete search history.

(56) References Cited

U.S. PATENT DOCUMENTS

| 10,022,277 | B2 * | 7/2018 | Heil | G06K 7/10366 |
| 2013/0041334 | A1 * | 2/2013 | Prioleau | A61F 13/42 604/361 |
| 2016/0120455 | A1 * | 5/2016 | Pop | A61B 5/6804 600/301 |
| 2018/0049926 | A1 * | 2/2018 | Lin Charna | A61B 5/1117 |
| 2018/0055697 | A1 * | 3/2018 | Mihali | A61F 13/42 |

* cited by examiner

*Primary Examiner* — Sarah B McPartlin
(74) *Attorney, Agent, or Firm* — Lanier Ford Shaver & Payne; Jeremy A. Smith

(57) ABSTRACT

The present subject matter relates to absorbent articles and signaling devices for use therewith. The signaling device can be configured to detect the presence of an insult in the absorbent article and/or in an undergarment. The signaling device can be further configured to determine whether the insult is a urine insult or a feces insult. The signaling device can provide a notification to a user that an insult has occurred and can inform the user whether the insult is a urine insult or a feces insult.

15 Claims, 2 Drawing Sheets

BODY FLUID SENSOR PAD

This is a continuation-in-part of U.S. Ser. No. 15/330,222 filed on Aug. 26, 2016 which claims benefit of U.S. provisional application No. 62/283,348 filed on Aug. 28, 2015.

FIELD OF THE INVENTION

The present invention relates to a signaling device configured to detect the presence of moisture in the absorbent article and/or in an undergarment. The signaling device can further wirelessly and/or visually provide notification to a nursing station and/or caregiver that an insult has occurred, thereby speeding up the response time for patient care.

BACKGROUND OF THE INVENTION

Decubitis ulcers, bed sores, and irritant diaper dematitis (IDD) occurs when continuous pressure, temperature, and body waste such as urine is in prolonged contact with skin. Deucbitis ulcers and bed sores are more frequent with the elderly or diabetic patients in home such as nursing homes or actute care facilities. IDD occurs frequently in babies due the sensitive nature of their skin. Frequent and prolonged skin contact with stool due to fecal incontinence and diarrhea are high risk factors for severe IDD. Many of these risks can be overcome by recent innovations in absorbent article technology, including absorbent articles having superabsorbent layers, reduced skin wetness, and superior pH control. The prevention of urine in contact with skin for a prolonged period, however, still poses a challenge. For instance, many absorbent articles include hydrophobic liquid permeable inner layers that permit urine to pass through the layer so that the urine does not contact the skin even after multiple insults. However, many of these absorbent articles fail to completely protect the user against prolonged contact of body waste with the skin.

Absorbent articles such as bed pads, diapers, training pants, incontinence products, feminine hygiene products, swim undergarments, and the like conventionally include a liquid permeable body-side liner, a liquid impermeable outer cover, and an absorbent core. The absorbent core is typically located in between the outer cover and the liner for taking in and retaining liquids (e.g., urine) exuded by the wearer. Various types of moisture or wetness indicators have been suggested for use with absorbent articles. These wetness indicators, however, are complicated, costly and add additional burdens to an already overloaded caregiver.

The present invention provides a simple and cost-effective signaling device configured to detect the presence of moisture in a bed pad, absorbent article and/or in an undergarment. The signaling device wirelessly and/or visually provides notification to a nursing station and/or caregiver that an insult has occurred, thereby speeding up the response time for patient care. Alerting the care staff to perform timely pad/absorbent article changes reduces pad/absorbent article dermatitis/rash that can ultimately lead to skin issues. These alerts can be documented by time/date stamps that are automatically logged into a web portal that is managed by the healthcare facility or personal caregiver with the intention of providing statistical data as to when an event occurred and how long that patient was exposed to the insult before they receive attention.

SUMMARY OF THE INVENTION

The present invention relates to a signaling device configured to detect the presence of moisture in the absorbent article and/or in an undergarment. The signaling device can further wirelessly and/or visually provide notification to a nursing station and/or caregiver that an insult has occurred, thereby speeding up the response time for patient care. The signaling device can be imbedded or sewn into the absorbent article, or it can be removably affixed to the absorbent article.

BRIEF DESCRIPTION OF THE FIGURES

A full and enabling disclosure of the present invention, including the best mode thereof to one skilled in the art, is set forth more particularly in the remainder of the specification, including reference to the accompanying figures.

DETAILED DESCRIPTION OF THE INVENTION

Figure 1:
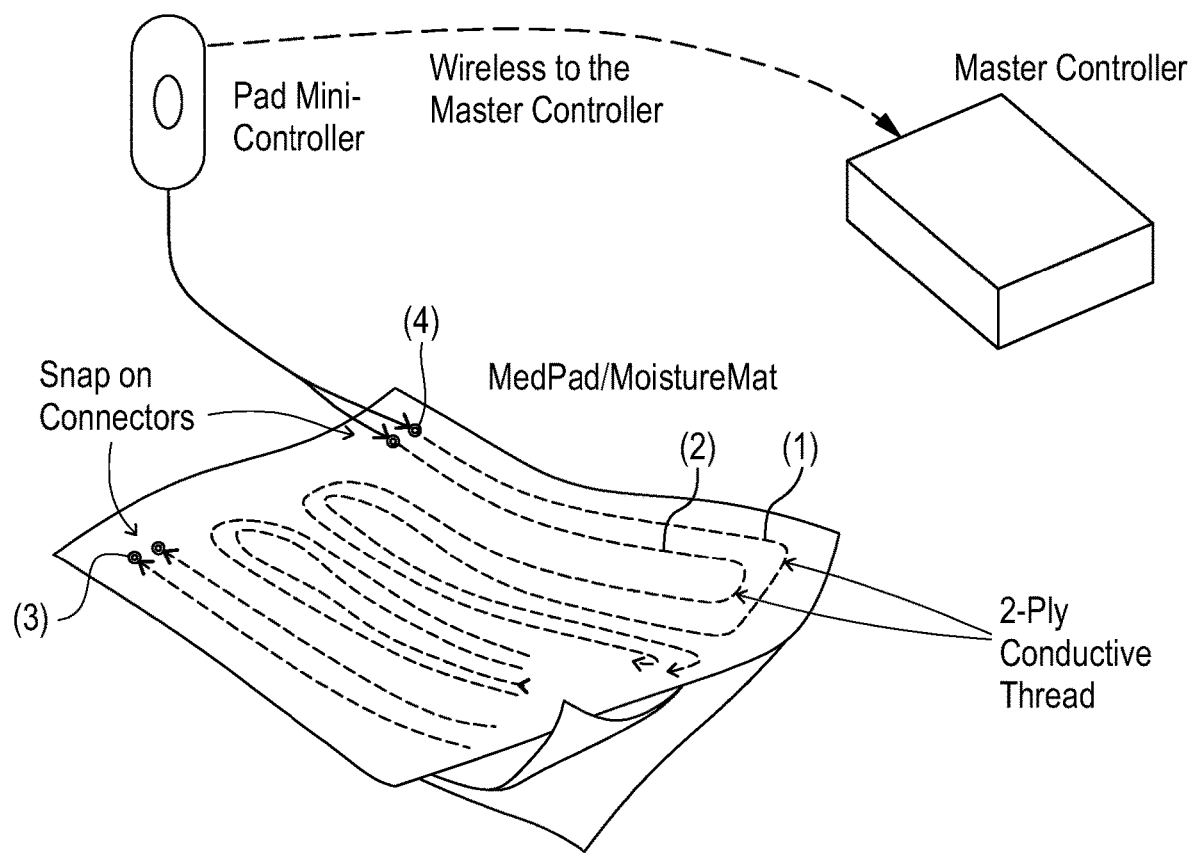
FIG. 1 is a perspective view of one embodiment of an absorbent article of the invention showing one possible sensor configuration.
Figure 2:
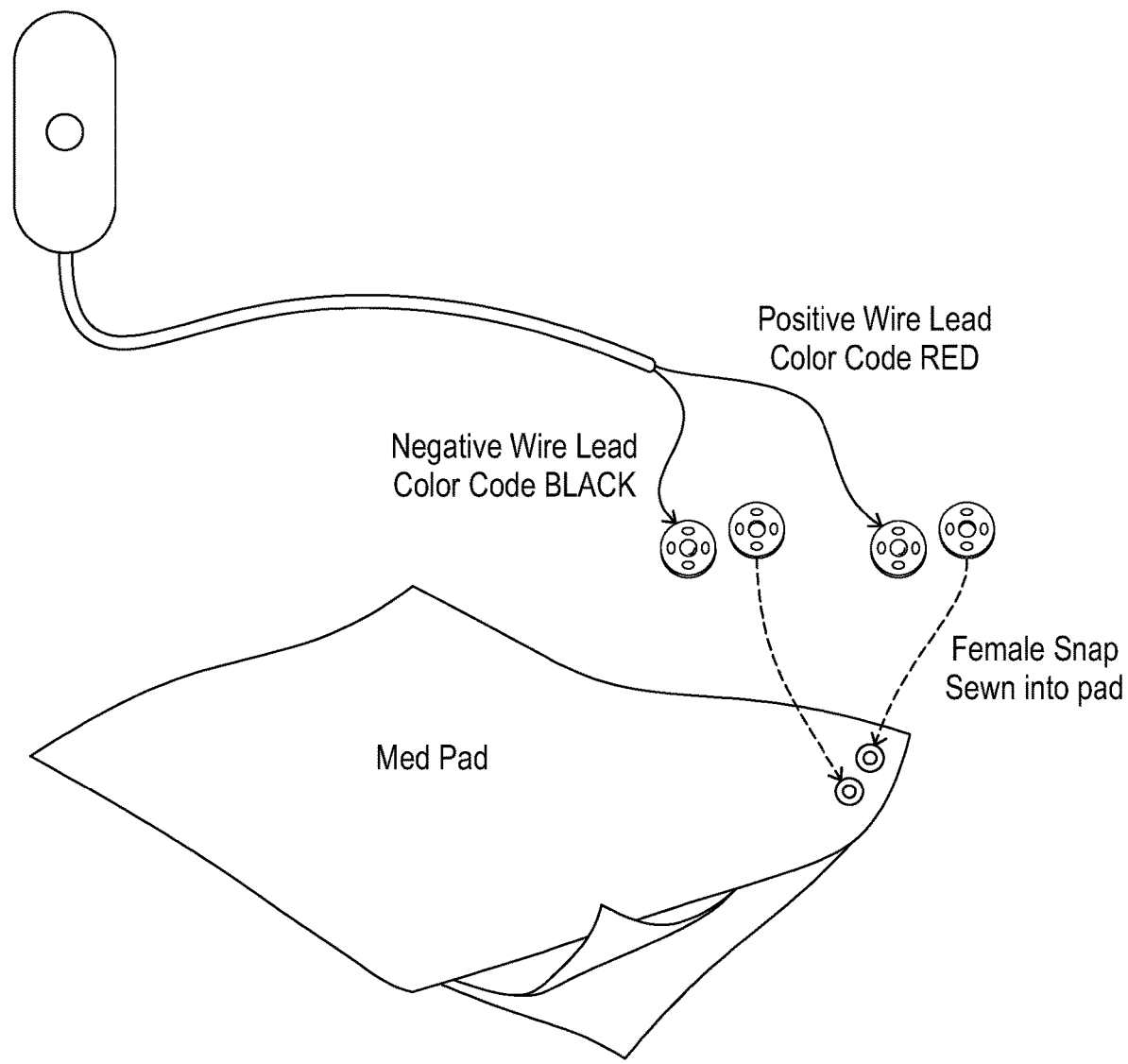
FIG. 2 is a front perspective view of the absorbent article according to an exemplary embodiment of the present disclosure.

The present invention generally provides a signaling device based on electrical detection using conductive elements separated by a distance on a substrate. In one embodiment, said substrate is on, within, is affixed to and/or comprises an absorbent article. These conductive elements are essentially wetness indicators that detect a change in an electrical property, such as impedance, due to the presence of an ionic liquid such as urine. The change in the electrical property triggers a signal or alarm to indicate the presence of wetness in the absorbent article.

In one embodiment, the invention relates to a signaling device for detecting an insult in an absorbent article. The signaling device includes a sensor configured to provide an output signal associated with an electrical property of the absorbent article. The electrical property changes in response to an insult. The signaling device further includes an electronic circuit coupled to the sensor.

In another embodiment, the signaling device is imbedded or sewn into the absorbent article. In another embodiment, the signaling device is removably affixed to the absorbent article.

In yet another embodiment, the invention is directed to a method for detecting and identifying an insult in an absorbent article. The method includes monitoring an electrical property associated with the absorbent article, which changes in response to an insult.

The method further includes detecting a change in the electrical property to determine the presence of an insult; and notifying the care giver in a timely automated manner to reduce response time, and ultimately reduce the probability of ulcers, dermatitis, rash and other skin issues.

The signaling device of the invention is configured to detect the presence of bodily fluids in an absorbent article or in an undergarment, and to inform the care giver that an insult has occurred. The signaling device of the invention can emit an audible and/or a visual signal in order to indicate to the user that the signaling device has detected an insult. The audible signal, for instance, may be as simple as one or more beeps. Similarly; if the signaling device issues a visible signal, the visible signal may comprise one or more lights or an interactive display. Instill another embodiment, the signaling device may be configured to vibrate when the circuit within the absorbent article is closed. In some embodiments, the signaling device can use a selected combination or all of the signaling techniques including, but not limited to vibration, visible signals, audio signals, and communication with remote devices, such as a smart phone or an IP based network. The signaling device can further wirelessly provide notification to a nursing station and/or caregiver that an insult has occurred, thereby speeding up the response time for patient care.

Discussion of an exemplary embodiment of the invention will be made with reference to FIG. 1. While the discussion of this embodiment is made with reference to a bed pad, it is understood that the present disclosure is suitable for use with various other absorbent articles.

FIG. 1 is an illustration of the signaling device of the invention in the form of a bed pad. The bed pad can be constructed in various ways as are known in the art, but typically they contain two or more layers, including a top layer, one or more middle absorbent layers and optionally a moisture barrier layer. The top layer typically does not substantially absorb moisture and allows moisture to pass to one or more middle absorbent layers. The moisture barrier layer prevents moisture from passing to, for example, the mattress. The bed pad can be designed and constructed to be reusable, or disposable. In FIG. 1, the middle layer of said bed pad is stitched a first conductive element (1) spaced from a second conductive element (2) in a substantially parallel manner approximately ½ to to 1 inch apart starting at one corner of the pad where two metal cleats (3) are located and continuing back to the opposite corner of the pad making a 180 degree turn and continuing back to the opposite end of the pad.

As one of ordinary skill will understand, the conductive elements (1) and (2) can extend any length of the bed pad as desired and they can be in any configuration suitable to generate a signal in the presence of moisture. The conductive elements (1) and (2) can comprise any suitable conductive material, such as a conductive thread, printed conductive lines, conductive wires, conductive foil, conductive tape and the like. The first conductive element (1) does not intersect the second conductive element (2) in order to form an open circuit that may be closed, for instance, when a conductive fluid or material such as a urine insult or a feces insult, is positioned between the conductive elements. The end of each conductive element at the edge of the pad and is secured to two metal connectors or metal cleats (3) so that the pad can be tested by the care giver before each use. For testing, the care giver simply bridges the two cleats together with, for example, metal or a damp cloth when the pad is connected to a monitoring device. If the monitoring device flashes red, the pad is functional and ready for use. The distance between threads and the manner that they are stitched to said middle layer are non-limiting, and one of ordinary skill will recognize that the main importance is that a significant portion of said pad is traversed by said conductive thread. The distance between the conductive elements can, however, be varied in order to adjust moisture sensitivity.

Conductive elements (1) and (2) may be incorporated into the bed pad at any suitable location as long as the conductive elements are positioned so as to contact a body fluid that is exuded by a user. In this regard, the conductive elements (1) and (2) preferably lie inside the outer cover and above the absorbent layer of the bed pad.

The layers of the bed pad can be sewn together with conventional threads in standard patterns. It is important, however, that the bed pad layers be configured and sewn so that the two conductive threads do not contact each other when the pad is wrinkled and/or folded. In one embodiment the layers of the bed pad are quilted such that the conductive elements (1) and (2) do not and cannot contact each other. In this regard, the middle absorbent layer can actually comprise two or more separate absorbent layers, each comprising conductive elements 1 and 2 respectively, such that said conductive elements are separated optionally with an intermediate layer disposed in between said conductive elements such that they do not contact each other. The distance between the conductive threads or elements and the absorbing layer thickness influences the response time to an insult.

The conductive thread through the pad can be on the same layer, separate layers in a vertical formation with one thread over the other separated by material, or a vertical formation with an offset so the top thread is not directly above the bottom thread.

The conductive thread through the pad starts at the 2 primary magnetic connectors for wet detection and routes through the pad in a serpentine pattern. The far end of the threading terminates on the bottom side to 2 conductive elements that can be bridged for testing purposes to ensure conductivity through the threads from end to end.

At the starting point of said bed pad, the conductive elements are secured to two metal connectors or cleats (3) thus providing a conductive platform. The cleats are configured to allow attachment of a snap, clamp like or other attachment means. In one embodiment, this attachment means is a clamp-like device which can communicatively attach to the cleats on said bed pad. To this clamp will be attached a circuit board or controller that will capture data and relay same through either wired or wireless means, back to the caregiver for quick response. Alternatively, this circuit board or controller can be imbedded within or is a part of said clamp. The clamp can also optionally comprise a light such as an LED light or other visual notification means that will flash when the pad is wet and the circuit will also pass this alert, along with a time and date stamp when the event took place to the care giver. The circuit within the clamp can also optionally have the ability to recognize the room and/or patient that it is monitoring. The clamp and associated circuit can be powered by simple battery, i.e., for example, a watch battery, AA or AAA size battery, or by standard 110 AC power cord.

The signaling device of the invention comprises a water sensing mechanism formed by said first (1) and second conductive elements (2). As moisture or urine passes through the top layer of the bed pad, it soaks the middle absorbent layer. The urine conducts electric current between conductive element 1 and conductive element 2 completing the circuit and causing the alarm signal. This alarm signal can be configured to a microprocessor which can notify a user/nurse's station of where water is present. Ideally this microprocessor can be configured to a master controller which can receive signals from multiple bed pads.

In another embodiment the bed pad utilizes 3 magnetic connectors, in one embodiment 10 mm connectors, that are placed near the edge on the underside of the pad leaving the patient's view of the pad as a standard bed pad. This configuration also avoids having the patient lay directly on potentially uncomfortable components. The addition of the 3rd connector is utilized to detect whether or not the pad is connected to the bedside controller or not. This connector is connected via conductive thread to the middle connector which acts as the ground to generate a second loop for detection purposes.

A version of the bed pad can also contain pressure/occupancy detection sensors in combination with the wetness detection. This is accomplished by using a bottom layer of conductive thread acting as left/right detection pockets. These are separated from the ground thread in the layer above by a resistive material similar to a sponge so that the ground and the left/right threads are only contacting under pressure such as the occupant's weight. This can also be a standalone pad for occupancy/pressure detection only or placed underneath the standard MedPad™ Bed Pad as an add-on.

In another embodiment, the bed pad of the invention can comprise wetness detection circuits, conductive tags, chips and the like that both detect moisture and relay a signal or alarm to the caregiver.

In another embodiment the moisture monitoring system comprises a bedside controller that is utilizes low power logic, in one embodiment one or more batteries, to provide a runtime of 2+ years. The battery is in an accessible separate compartment of the housing allowing for easy replacement of the battery when needed. In another embodiment he bedside controller optionally includes voltage reference monitoring for providing battery life statistics and alarms. In another embodiment the bedside controller optionally includes a manual "test" button so nurses performing routine check-ins can manual press a button to check for wetness if desired. In one embodiment this button lights up a green LED for dry and a red LED for wet. The bedside controller can include 2 I/O pins for wetness detection and bed pad detection or if pressure sensors are included 4 I/O pins for wetness detection, bed pad detection, pressure left detection, pressure right detection.

In another embodiment the bedside controller optionally includes a RP-SMA connector for connecting a small external antenna to increase transmission range if needed.

In still another embodiment all data transmission from the Bedside Controller through the rest of the MedPad™ network is achieved over the 802.15.4 standard on a completely isolated, private network.

The bedside controller can route its messages through any available node on the MedPad™ network and adapt in real time if a standard path becomes unavailable. Routing available through: A MedPad AP, another bedside controller awake and in range, or directly to the Master Controller. The bedside controller connects to the bed pad via a replaceable lanyard style harness. The harness has a quick disconnect connector on the Bedside Controller end and a magnetic connection on the bed pad end.

MedPad APs act as always on message repeaters for areas where the Bedside Controller cannot communicate directly with the master controller. The MedPad AP allows the Bedside Controllers to be able to sleep for battery preservation instead of having to be powered on at all times to route messages room to room from other Bedside Controllers. MedPad AP is an optional POE or DC powered device with an adjustable external RP-SMA antenna. As one readily recognizes, MedPad AP can be ceiling mounted, wall mounted, or placed on a flat surface.

The Master Controller is a server which bridges the private MedPad network to your typical IP based network to provide data to the MedPad Cloud and local devices over the corporate network. The Master Controller is the end and start point for ALL messages within the MedPad network and handles all processing.

The Master Controller is a small micro PC utilizing traditional network interfaces (Wireless & Ethernet) in addition to the 802.15.4 standard utilized by all MedPad devices.

The Master Controller optionally has an adjustable external antenna for increasing range on the MedPad network.

In one embodiment the Master Controller runs a local web server to provide users access to the MedPad data regardless of internet connection. This data can be accessed via a dashboard on a computer web browser, a mobile app, or can be live updated on a monitoring screen.

The bed pad (1) can be disposable or not. The bed pad can be fabricated to survive several wash cycles and normal wear and tear associated with typical use. Once completely dry, the bed pad will be able to be put back into use with the same monitoring accuracies.

The signaling device can be a separate article that is placed on or affixed to said bed pad by adhesive means, for example, by adhesive backing, double sided tape, Velcro fastening and the like. In this embodiment, a felt pad or other suitable textile material of construction is stitched in a manner similar to the way the middle layer is stitched in the bed pad. The article can be of varied shape, e.g., circular, square, rectangular, and the like. More specifically, the two conductive elements (1) and (2) can be two ply conductive thread or other conductive material sewn in a substantially parallel manner approximately ½ to to 1 inch apart starting at one corner of the pad where two metal cleats (3) are located and continuing back to the opposite corner of the article making a 180 degree turn and continuing back to the opposite end of the article. The end of each thread ends at the edge of the article and is secured to two metal cleats (4) so that the article can be tested by the care giver before each use. In this embodiment, the signaling device/article can have an adhesive backing that can be easily and quickly affixed to a conventional bed pad and/or absorbent article.

The invention also contemplates a MedPad network which can obtain, compile and/or provide the user with an enormous amount of data that can be toggled to the user/network preferences. For example, the MedPad system can send alerts via: SMS/Text, email, automated phone calls, live dashboard, mobile app notification, and/or computer software notification. Optionally, the MedPad network can provide alerting on the following critical items: when the bed pad becomes wet, how long the bed pad was wet, when the bed pad has been changed, when the bed pad is connected or disconnected, when a patient gets out of bed, when a patient returns to the bed, whether a patient is laying on his/her back, on their left side, on the right side, and for how long, when the bedside controller battery is low on power, when a bedside controller goes offline or comes online, when a MedPad AP has goes offline, or comes online, when a bedside controller is moved from its original location, and the general health of all hardware components of the Bedside Controller, MedPad AP and/or Master Controller. Reports can be generated providing a full log of all events and timestamps within the MedPad network.

In another embodiment the invention comprises MedPad applications which are split into three different parts. The front-end user interface, back-end server and the local server.

The front-end user interface is what the end users see. This is a combination of web applications and mobile applications that act as an interactive layer between the user and the servers. The different "versions" of the application will be controlled by user account permissions. Facility owners, doctors and nurses will have access and see more data than family members. However, it will be the same application; just certain elements will be hidden based on which user is signed in and which server they're connected to.

The local server nodes will be hosted devices inside various facilities that subscribe to our product. The reason for this design is so that each facility can operate the application regardless of internet connection. Keeping the system functional in times of an outage. The local server will also be setup in such a way to forward data securely to our back-end server. Have local server nodes give us redundancy as well as increased security when posting data to the back-end server.

The back-end server will be hosted and accessible publicly—but locked behind logins and security. The reason for this is to have a way for the data to be accessible outside of the hospitals over the internet by using the MedPad mobile apps and websites. The back-end layer is also where the main API is hosted and controlled.

Data flow refers to how the overall process for how the data will flow is the physical MedPad devices will send data to the local server; The local server will store the data and any devices connected locally running the Applications will be able to access the data on the local server. To get the data to the families and people outside of the local environment—the local server will post the data to the back-end server. The back-end server will then store records and also act as a data back-up for the local server in the case of any failures on-site.

While the discussion of the exemplary embodiment are made with reference to a bed pad, it is understood that the present disclosure is suitable for use with various other absorbent articles intended for personal use and/or wear, including but not limited to diapers, training pants, swim pants, feminine hygiene products, incontinence products, medical garments, surgical pads and bandages, other personal care or health care garments, and the like without departing from the scope of the present disclosure. It should also be understood the various exemplary embodiments could also be used to identify and classify an insult in an undergarment if a user would like to monitor the presence of an insult without necessarily requiring an absorbent article.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged in whole, or in part. Furthermore, those of ordinary skill in the art will appreciate that the foregoing description is by way of example only and is not intended to limit the invention so further described in such appended claims.

What is claimed:

1. An absorbent article comprising a signaling device for detecting and identifying a moisture insult, the signaling device comprising:
   a substrate;
   a first absorbent layer;
   a second absorbent layer; and
   a moisture sensor, wherein said sensor comprises a first and second conductive element, wherein said first absorbent layer comprises said first conductive element having a first length and a first metal connector on a first end of said first conductive element; wherein the second absorbent layer comprises a second conductive element having a second length and a second metal connector on a first end of said second conductive element;
   wherein the first conductive element and the second conductive element are disposed on the first and second absorbent layers respectively such that said first and second conductive elements do not contact each other thereby forming an open circuit;
   wherein the first and second metal connectors provide a conductive platform configured to allow power to be supplied to the open circuit through the metal connectors; wherein the first and second conductive elements form an open circuit under dry conditions and wherein said open circuit is completed in the presence of a moisture insult causing an alarm signal indicating the presence of said insult.

2. The absorbent article of claim 1 wherein said article has an adhesive backing.

3. The absorbent article of claim 1 wherein the alarm signal is transmitted to a caregiver or nursing station.

4. The absorbent article of claim 1 further comprising a moisture barrier layer.

5. The absorbent article of claim 1 wherein said insult is urine.

6. The absorbent article of claim 1 wherein said alarm signal is a visual or audible signal.

7. The absorbent article of claim 1 wherein said alarm signal is transmitted to a remote device.

8. The absorbent article of claim 7 wherein said device is a smart phone or an IP based network.

9. The absorbent article of claim 1 wherein said open circuit is powered by a battery or an AC power source.

10. The absorbent article of claim 1 wherein said article is a bed pad.

11. The absorbent article of claim 1 wherein said first and second conductive elements comprise conductive thread, printed conductive lines, conductive wires, conductive foil, conductive tape or a combination thereof.

12. The absorbent article of claim 1 wherein said first and second metal connectors are a cleat, a clamp or a snap.

13. A system for detecting the presence of bodily fluids comprising a plurality of bed pads connected to a power source, wherein each bed pad comprises a signaling device comprising:
   a substrate;
   a first absorbent layer;
   a second absorbent layer; and
   a moisture sensor, wherein said sensor comprises a first and second conductive element, wherein said first absorbent layer comprises said first conductive element having a first length and a first metal connector on a first end of said first conductive element; wherein the second absorbent layer comprises a second conductive element having a second length and a second metal connector on a first end of said second conductive element;
   wherein the first conductive element and the second conductive element are disposed on the first and second absorbent layers respectively such that said first and second conductive elements do not contact each other thereby forming an open circuit;
   wherein the first and second metal attachment means provide a conductive platform configured to allow power to be supplied to the open circuit through the metal connectors; wherein the first and second conductive elements form an open circuit under dry conditions and wherein said open circuit is completed in the presence of a moisture insult causing an alarm signal indicating the presence of said insult.

14. The system of claim 13, wherein said alarm signal is transmitted to a smart phone, an IP based network and/or a caregiver's or nurse's station.

15. The system of claim 13 wherein said first and second metal connectors are a cleat, a clamp or a snap.

\* \* \* \* \*